United States Patent
Conte et al.

[11] Patent Number: 6,027,748
[45] Date of Patent: Feb. 22, 2000

[54] PHARMACEUTICAL TABLET, COMPLETELY COATED, FOR CONTROLLED RELEASE OF ACTIVE PRINCIPLES THAT PRESENT PROBLEMS OF BIO-AVAILABILITY LINKED TO GASTRO-INTESTINAL ABSORPTION

[75] Inventors: Ubaldo Conte, Busto Arsizio; Lauretta Maggi, Pavia, both of Italy; Pascal Grenier; Guy Vergnault, both of St. Louis, France; Robert Zimmer, Mulhouse, France

[73] Assignee: Jagotec AG, Hergiswill, Switzerland

[21] Appl. No.: 09/003,406

[22] Filed: Jan. 6, 1998

[30] Foreign Application Priority Data

Jan. 8, 1997 [IT] Italy .................. MI97A0016

[51] Int. Cl.⁷ .................. A61K 9/32; A61K 9/36; A61K 9/58; A61K 9/62
[52] U.S. Cl. .................. 424/458; 424/451; 424/452; 424/456; 424/457; 424/468; 424/461; 424/462; 424/480; 424/482; 424/472; 514/772.2; 514/772.3; 514/777; 514/778; 514/785; 514/786
[58] Field of Search .................. 424/480, 481, 424/482, 475, 458, 459, 461, 462, 468, 451, 452, 456, 457, 472

[56] References Cited

U.S. PATENT DOCUMENTS 4,933,186  6/1990  Ohm et al. .................. 424/476

*Primary Examiner*—Thurman K. Page
*Assistant Examiner*—James M. Spear
*Attorney, Agent, or Firm*—Abelman, Frayne & Schwab

[57] ABSTRACT

Described herein is a particular type of pharmaceutical tablet, for oral use, which is formed by one or more layers, and is specifically designed for controlled release of active principles that present problems of bio-availability linked to absorption in the gastro-intestinal tract, and in particular active principles that present an erratic and unpredictable absorption linked to the presence or absence of food at the level of the stomach and/or of the first portion of the small intestine, the said pharmaceutical form being characterized in that it is completely coated with one or more films of a biocompatible and biodegradable polymeric material.

15 Claims, 1 Drawing Sheet

PHARMACEUTICAL TABLET, COMPLETELY COATED, FOR CONTROLLED RELEASE OF ACTIVE PRINCIPLES THAT PRESENT PROBLEMS OF BIO-AVAILABILITY LINKED TO GASTRO-INTESTINAL ABSORPTION

INTRODUCTION AND PRIOR ART

Modern pharmaceutical technology has developed a considerable number of new controlled-release pharmaceutical forms (i.e., pharmaceutical forms with immediate release or prolonged release, either slowed down or in some way modified), and, in general, therapeutic systems capable of releasing an active principle vehicled in them in either short or protracted periods of time have been designed and developed.

A fundamental characteristic of all slow-release pharmaceutical forms, of those more generically indicated as "delay" forms, is the fact that they require the vehicling of a high quantity of active principle which, when the system functions correctly, is released gradually by the latter, so that it carries on its activity for a prolonged period of time.

The fields of application of controlled release are highly diversified in that they include the agricultural sector (for insect repellents and fertilizers) and the sector of cosmetics; however, a very extensive development has also taken place in the pharmaceutical sector. It is in this area, in fact, that there is a particularly strongly felt need to have available "release systems" capable of releasing the active principle, in the case in point a drug, over a prolonged period of time and at a rate suitable for bringing about and maintaining high and effective blood plasma concentrations of the drug.

As mentioned above, for all the fields of application, but above all for the pharmaceutical sector, systems for the gradual (or controlled) release of the active principle require the vehicling of the latter in high quantities in so far as the period of effectiveness envisaged for the system is longer.

Numerous systems have been developed and put on the market up to the present moment for the purpose of obtaining a prolonged "therapeutic cover", i.e., the maintenance of therapeutically effective plasma levels of the active principle, and for reducing the number of daily administrations. Examples of the such are the so-called matrix systems, the "reservoir" systems, the osmotic pumps (known by the trade-mark "OROS"), and the "push-pull" systems, as well as the more traditional pharmaceutical forms, such as those consisting of capsules containing chronoids. However, alongside the undoubted advantages which these systems, when operating correctly, bring with them, there are numerous limitations and drawbacks due above all to the control mechanism, and hence to the in vivo functioning of the system, which can drastically limit and/or totally nullify the therapeutic effect obtained from the administration of the pharmaceutical form.

For prolonged-release forms, which serve as vehicles of at times very high quantities of active principle, the release of an excessive fraction of the latter within a short lapse of time (a phenomenon referred to as "dose dumping") is particularly delicate and critical. The above phenomenon of dose dumping may occur mainly immediately after the administration of the therapeutic system and is particularly evident in the case of oral administration.

Albeit without reaching irreversible toxic effects, many protracted-release pharmaceutical forms or therapeutic systems for oral use are commonly characterized by a more or less evident initial dose-dumping phase, which leads to side effects that are reversible but, in any case, badly tolerated by the patient. It should moreover be emphasized that in some therapeutic systems, the method for controlling the release of the drug consists in applying a polymer coating. For example, in the osmotic pump, known as the OROS system, the coating consists of polymeric materials that are insoluble and non-biodegradable in the gastro-intestinal tract, and this fact may lead, as recently occurred in a number of patients, to phenomena of accumulation of the emptied envelopes in the intestine, with serious consequences and the risk of intestinal occlusion, the latter being an event that has already been reported in the specialized literature of the sector.

Other types of therapeutic systems which function by means of different mechanisms and with different possibilities of use have been described in the literature, developed, and put on the market. Amongst such systems are the so-called gellable hydrophilic matrices, which are widely used in the therapeutic field, characterized, however, by the fact that the fraction of drug present on the surface of the matrix is released more rapidly, before the retarding polymer reaches its full degree of efficiency. In such cases, in the first hour approximately 20–40% of the drug may be released. This phenomenon of dose dumping may lead to side effects linked to the specific active principle administered.

For all controlled-release pharmaceutical forms, another drawback, which is more difficult to foresee, is instead linked to the biological processes of absorption of the active principle released by the therapeutic system. In particular, the concomitant administration of food may have a considerable effect on the extent and rate of absorption of the active principle of which the pharmaceutical form provides the vehicle. This situation is usually defined as the "food effect". The latter phenomenon may be revealed only with numerous and complex tests on healthy volunteers or with equally complex clinical assessments conducted in a rigorously controlled manner.

In particular, it has recently been highlighted that for numerous active principles, such as nifedipine and ketoprofen, the processes of absorption of the active principle are dramatically affected by the presence of food at the level of the stomach and of the first portion of the small intestine.

After the oral administration of controlled-release pharmaceutical forms, the absorption of these active principles occurs in an anomalous and non-predictable manner, which depends largely upon the physiological conditions of the gastro-intestinal tract, thus determining blood plasma levels that may be extremely variable from one subject to another. This may lead to erratic and altogether non-reproducible therapeutic effects.

DESCRIPTION OF THE INVENTION

It has now been unexpectedly found, and this finding forms the subject of the present industrial patent application, that, using precise production technologies that are industrially highly reproducible, it is possible to produce therapeutic systems that do not cause dose dumping and that, above all, enable the problems of variability and unpredictability involved in absorption due to the presence or absence of food in the gastrointestinal tract to be overcome; i.e., a new therapeutic system has been developed and experimented which simultaneously solves the problems linked to dose dumping and those linked to the food effect.

A pharmaceutical form has above all been obtained which presents innovative advantages of safety and therapeutic effectiveness, in that the food effect is completely eliminated; i.e., the absorption of the active principle takes place in a reproducible way either in the presence or in the absence of food.

It has in fact been found, and this finding likewise forms the subject of the present invention, that by applying a film of biocompatible and biodegradable polymeric material on a pharmaceutical form serving as vehicle of the active principle, it is possible to obtain in vivo kinetics of absorption characterized by reduced variability and not influenced by the presence of food (food effect). In addition, it is possible to obtain a delay in the initial phase of release of the active principle, thus avoiding an excessively rapid release (dose dumping) of the active principle.

This result may be highlighted by the determination of the blood plasma levels of the drug obtainable after administration of the new coated tablet, as claimed in the present patent, to healthy volunteers both in fasting conditions and after a standardized meal.

In a typical embodiment (as will be better defined in the examples provided in the present patent application), the new finding has the appearance of a rounded tablet, which contains the active principle. Typically, but not necessarily, the tablet may have one, two, or three layers, one of which serves as vehicle of the drug, whilst the other layer, or the other two layers, have exclusively the function of barriers limiting release, as described and claimed in the U.S. Pat. No. 4,839,177 (1989), and above all in the subsequent U.S. Pat. No. 5,422,123 (1995).

The present invention, however, is characterized by the fact that the aforesaid tablet, which serves as vehicle for the said active principle that presents problems of variability and unpredictability of absorption, undergoes a process of film-coating with a biocompatible and biodegradable, preferably gastro-resistant, polymeric material, using consolidated production processes that guarantee high yield and are altogether acceptable from the pharmaceutical point of view.

A consequence of these characteristics is the total absence of the dose-dumping phenomenon, as well as the possibility of designing therapeutic systems that present release profiles that may be pre-programmed according to the specific therapeutic requirements sought for a given active principle.

The therapeutic form that is the subject of the present patent application consists of a coated tablet containing, in addition to the active principle, suitable excipients. One or more of the said pharmaceutical forms may be contained in capsules of hard gelatine with the aim of vehicling the desired quantities of active principle. The tablets that are the subject of the present patent application (see FIG. 1) are characterized in that they are rounded, so as to facilitate the film-coating process, and in that they have diameters of from 2 to 13 mm, and preferably of from 4 to 10 mm, and a thickness of from 2 to 8 mm, and preferably of from 3 to 6 mm.

One of the characteristics of the tablet of the invention consists in the fact that, in the preparation of the core of the tablet containing the active principle, polymeric substances are used that are capable of modulating (i.e., slowing down and/or speeding up) release of the active principle.

As active principles the following may be employed: steroid anti-inflammatory drugs, such as dexamethasone, hydrocortisone and methylprednisolone, or non-steroidal anti-inflammatory drugs (NSAIDs), such as sodium diclofenac, indomethacin, ibuprofen, ketoprofen, diflunisal, piroxicam, naproxen, flurbiprofen, sodium tolmetin, or sleep-inducing drugs and tranquillizers, such as diazepam, nitrazepam, flurazepam, oxazepam, chlordiazepoxide, medazepam, lorazepam, or active principles for the prevention of attacks of angina, such as nifedipine, nitrendipine, nicardipine, or antihistamine and/or anti-asthmatic drugs, such as ephedrine, terfenadine, theophylline, chlorpheniramine, or antibiotics, such as ampicillin, amoxicillin, cephadrine, their salts or derivatives, and in particular in association with β-lactamase inhibitors, such as clavulanic acid.

The polymer substances used in the preparation of the tablet are chosen in the group comprising hydroxypropylmethyl cellulose with molecular weight of between 1,000 and 4,000,000, hydroxypropyl cellulose with molecular weight of from 2,000 to 2,000,000, carboxyvinyl polymers, polyvinyl alcohols, glucans, scleroglucans, mannans, xanthans, alginic acid and its derivatives, polyanhydrides, polyaminoacids, carboxymethyl cellulose, cross-linked sodium carboxymethyl cellulose, polyvinyl pyrrolidone, cross-linked polyvinyl pyrrolidone, carboxymethylamide, potassium methacrylate/divinylbenzene copolymer, starches and their derivatives, β-cyclodextrin, dextrin derivatives in general with linear or branched chains, ethyl cellulose, methyl cellulose and cellulose derivatives in general. Said polymer substances are present in a percentage of from 5% to 90% with respect to the total weight of the tablet, and preferably of from 10% to 50%.

Of all the polymers referred to above, there are available on the market various types characterized by different chemico-physical characteristics as well as characteristics regarding solubility and gel formation; in particular, as far as hydroxypropylmethyl cellulose is concerned, various types may be used having different molecular weights (of from 1,000 to 4,000,000) and different degrees of substitution. Said types of hydroxypropylmethyl cellulose present different characteristics, being prevalently erodible or prevalently gellable according to the viscosity and the degree of substitution (DS) that they present in the polymer chain. The adjuvating substances are chosen in the group comprising glyceryl monostearate and its semi-synthetic triglyceride derivatives, semi-synthetic glycerides, hydrogenated castor oil, glyceryl palmitostearate, glyceryl behenate, ethyl alcohol, polyvinyl pyrrolidone, glycerin, ethyl cellulose, methyl cellulose, sodium carboxylmethyl cellulose, magnesium stearate, stearic acid, talcum, sodium benzoate, boric acid, polyoxyethylene glycols, and colloidal silica, as well as other natural or synthetic substances that are well known to those skilled in the sector.

The following substances may moreover be employed: diluents, binders, lubricants, buffering agents, anti-adherent agents, gliding agents, as well as other substances capable of bestowing on the said layer the desired characteristics, as will be illustrated in greater detail by the examples given in the sequel.

The plasticizing substances are chosen from the group comprising hydrogenated castor oil, cetyl alcohol, cetyl-stearyl alcohol, fatty acids, glycerides and triglycerides as such or variously substituted, and polyoxyethylene glycols and their derivatives having different molecular weights, normally chosen in the 400–6,000,000 range. These have the function of conferring on the formulation the required elasticity and of improving the characteristics of compressibility, adhesion and cohesion.

Finally, excipients may be used that are commonly employed in pharmaceutical techniques, such as mannitol, lactose, sorbitol, xylitol, talcum, magnesium stearate, colloidal silica, as well as glyceryl monostearate, hydrogenated castor oil, waxes, and mono-, bi- and tri-substituted glycerides.

When the aim is to favour the penetration of water and/or aqueous fluids into the layer serving as vehicle of the active principle or core, hydrophilic diluents are introduced, such as mannitol, lactose, starches of various origin, sorbitol, xylitol, or else surfactants, wetting substances and/or substances generally favouring water penetration into the compact are introduced into the formulation.

When, instead, the aim is to slow down the penetration of water and/or aqueous fluids into the layer serving as vehicle of the active principle or core, hydrophobic diluents are introduced, such as glyceryl monostearate, glyceryl behenate, hydrogenated castor oil, waxes, and mono-, bi- and tri-substituted glycerides.

The pharmaceutical tablets of the invention have the advantage of releasing the vehicled active principle in a programmed manner; hence, it is possible to vehicle an appropriate amount of the drug, thus preventing the dose-dumping phenomenon and meeting specific therapeutic requirements by means of the controlled release of the active principle vehicled. In the simplest embodiment, the system appears as shown in FIG. 1, i.e., as a tablet coated with one or more layers, at least one of which contains the active principle suitably vehicled. Alternatively this core could consist of a tablet as described in the U.S. Pat. No. 5,422,123; namely, a system with one or more barriers that limit the portion of the surface of the layer containing the active principle that is exposed to the dissolution means (FIG. 1b and FIG. 1c). This portion accounts, on average, for 50–70% of the total surface of the tablet, and it is therefore only from this limited surface that the active principle can be released in the initial phase of contact with the dissolution means after the protection of the coating has been removed.

It should be pointed out that, if the system is one with two barrier layers, as shown in FIG. 1c, the surface from which the active principle is initially released is more limited, and generally accounts for 20–50% of the total area of the pharmaceutical form.

A fundamental characteristic for obtaining the desired therapeutic effect is the fact that on the tablet according to the invention is applied a film of biocompatible and biodegradable polymeric material, or one or more coating films of different compositions may be applied.

For the coating of the tablet, the following materials may be preferably used: polymeric materials, such as derivatives of cellulose (hydroxypropylmethyl cellulose, hydroxyethyl cellulose, hydroxypropyl cellulose, and their respective derivatives), polymers of alginic acid and its salts and derivatives, derivatives of acrylic and methacrylic acid, polymers and copolymers of said acids and/or their respective esters, which present different degrees of permeability according to their chemico-physical properties; for example, copolymers synthesized from esters of acrylic and methacrylic acid with a low content of quaternary ammonium groups. The molar ratio of these ammonium groups with respect to the remaining neutral portions of esters of (meth) acrylic acid may range from 1:20 to 1:40, whilst the molecular weight is approximately 150,000.

To obtain gastro-resistance, polymeric materials may be used, such as cellulose acetophthalate, cellulose acetopropionate, cellulose trimellitate, methylvinyl ether-maleic anhydride copolymer, dibutyl phthalate, acrylic and methacrylic polymers and copolymers, having different molecular weights and degrees of solubility depending on their different pH values; for example, anionic-type copolymers consisting of methacrylic acid and methyl ester of methacrylic acid where the ratio between the free carboxyl groups and the esterified groups may range from 1:1 to 1:2, whilst the molecular weight is approximately 135,000.

The said coating is of the gastro-resistant and entero-soluble type, so as to enable activation of the system only after the tablet has reached the duodeno-intestinal tract, or else with pH-dependent solubility, which enables release of the active principle when the pH in the stomach exceeds a given threshold value on account of the presence of food.

Said materials may be applied on the finished pharmaceutical form by means of the classical process of film-coating using said polymers in a solution of organic solvents, but preferably in aqueous dispersion and operating by means of nebulization in a revolving pan or in a fluidized bed.

The said materials may be used in association with other retarding polymers or with the addition of other adjuvants, such as lactose starch, colouring agents, such as iron oxides, opacifying agents, such as talcum and titanium dioxide, and sweeteners. The invention is moreover characterized in that, in the film-coating phase, a plasticizing agent is used, preferably triethyl citrate, diethyl phthalate, diacetin, triacetin, dibutyl phthalate, dibutyl tartrate, tributyl acetate, castor oil, cetyl alcohol, cetylstearyl alcohol, fatty acids, glycerides and triglycerides as such or variously substituted, polyoxyethylene glycols in different percentages with respect to the polymeric material of the coating, but preferably in percentages of between 10% and 20%.

The examples, and the results obtained in the experimental forms described, provide a better illustration of the characteristics and working of the new system. In any case, the innovative feature of the embodiment is characterized by the fact that it is possible to obtain the claimed therapeutic system using currently applied production technologies; i.e., the system is immediately transferable to industrial production.

BRIEF DESCRIPTION OF THE DRAWINGS

FIG. 1-a represents the pharmaceutical tablet according to the present invention not containing the barrier layer and wherein 1 indicates the core containing the active ingredient and 2 represents the coating layer according to the present invention.

FIG. 1-b represents the pharmaceutical tablet according to the present invention containing only one barrier layer and wherein 1 indicates the coating layer according to the present invention 2 indicates the core layer containing the active ingredient, 3 indicates the barrier layer.

FIG. 1-c represents the pharmaceutical tablet according to the present invention wherein the core layer is placed between two barrier layers and wherein 1 indicates the coating layer according to the present invention, 2 indicates the core layer containing the active ingredient and 3' and 3" indicate, respectively, the upper and lower barrier layers.

EXAMPLE 1

Figure 1A:
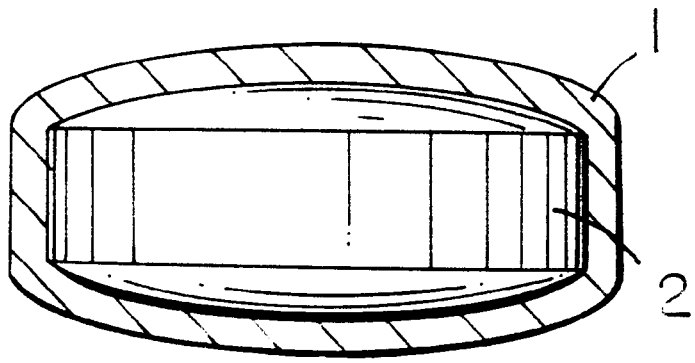
FIG. 1 represent some preferred embodiments of the tablet according to the present invention containing only one coating layer.
Figure 1B:
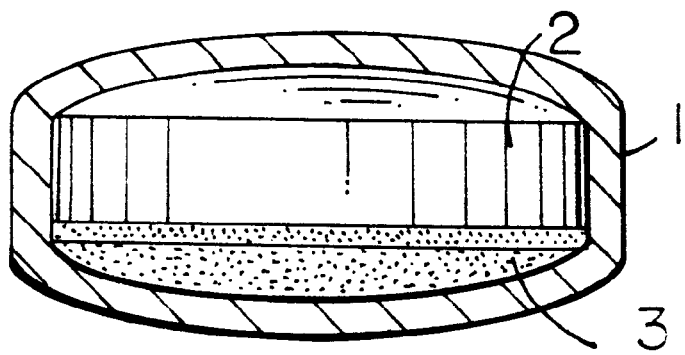
Figure 1C:
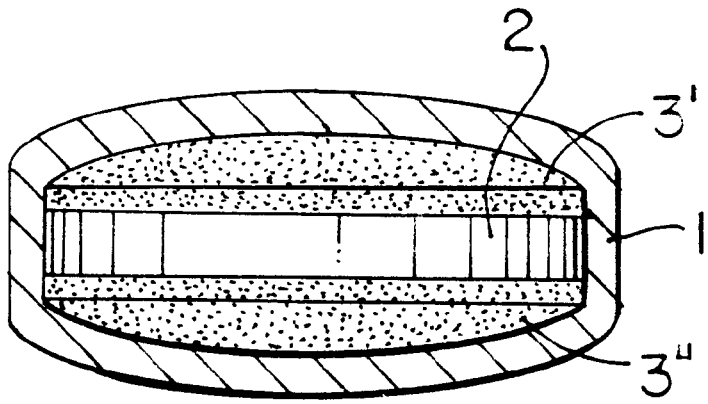

Preparation of a batch of 5,000 tablets, of the type shown in FIG. 1-b, containing 60 mg of nifedipine as active principle.

1-a-Preparation of Granulate Containing the Active Principle

A granulate is prepared according to the procedure described hereinafter, which is used in the preparation of layer 2 of FIG. 1-b.

The layer contains 60 mg of active principle and presents the following composition per unit:

| | |
|---|---|
| Nifedipine (Industrie Chimiche Ital., batch 3671) | 60.0 mg |
| Lactose monohydrate (USP grade, Carlo Erba, Milan, It.) | 30.0 mg |
| Hydroxypropylmethyl cellulose (Methocel K 100 M, Colorcon, Orpington, UK) | 30.0 mg |
| Polyvinyl pyrrolidone (Plasdone ® K29-32, I.S.P., Wayne, NY, USA) | 10.0 mg |
| Sodium laurylsulphate (Carlo Erba, Milan, Italy) | 10.0 mg |
| Magnesium stearate (Carlo Erba, Milan, Italy) | 2.0 mg |
| Colloidal silica (Syloid 244, Grace GmbH, Worms, Germ.) | 2.0 mg |
| Total | 144.0 mg |

The production process consists in preparing a granulate obtained by mixing the appropriate quantities of nifedipine, lactose and hydroxypropylmethyl cellulose in a sigma mixer, Mod. Erweka, type K5 (Frankfurt am Main, Germany). The homogeneous mixture of powders is wetted with a 10% (wt/vol) polyvinyl pyrrolidone aqueous solution in which the sodium laurylsulphate has been solubilized. The mass, homogeneously wetted, is forced through a 25-mesh (710 μm) grill to obtain a regular granulate, which is dried in a fluidized-bed apparatus (Aeromatic Mod. Strea) with incoming air temperature of 40–45° C. The granulate, which is dried until constant weight is achieved, is next put in a powder mixer Turbula Mod. T2A (Bachofen, Basel, Switzerland), with the addition of magnesium stearate and colloidal silica, and then mixed for a further 20 minutes. The granulate, lubricated, is analyzed as regards the content of active principle, and then undergoes a compression phase, as described later.

Said plasticizers may be present in a percentage of from 2% to 40%, preferably of from 10% to 40%, with respect to the polymeric coating material.

1-b-Preparation of the Granulate Forming the Barrier Layer

A quantity of granulate is prepared that is required for obtaining 5,000 barrier layers (layer No. 1 in FIG. 1-b), each of which has the following percentage composition::

| | |
|---|---|
| Hydroxypropylmethyl cellulose (Methocel ® .E 50 Premium, Colorcon, Orpington, UK) | 38.25 mg |
| Lactose monohydrate (USP grade, Carlo Erba, Milan, It.) | 38.25 mg |
| Glyceryl behenate (Compritol 888 ATO, Gattefossé, France) | 18.40 mg |
| Polyvinyl pyrrolidone (Plasdone ® K29-32, Gaf. Corp., Wayne, NY, USA) | 3.50 mg |
| Yellow iron oxide (Eingemann-Veronelli, Milan, Italy) | 0.10 mg |
| Magnesium stearate (USP grade, Carlo Erba, Milan, Italy) | 1.00 mg |
| Colloidal silica (Syloid 244, Grace GmbH, Worms, Germ.) | 0.50 mg |
| Total | 100.0 mg |

The production process consists in preparing a granulate obtained by mixing the appropriate quantities of hydroxypropylmethyl cellulose (Methocel E 50, viscosity 50 cps), glyceryl behenate and yellow iron oxide in a sigma mixer, Mod. Erweka, type K5 (Frankfurt am Main, Germany). The homogeneous mixture of powders is wetted with a 20% (wt/vol) polyvinyl pyrrolidone aqueous solution, and the mass, homogeneously wetted, is forced through a 25-mesh (710 μm) grill to obtain a light yellow regular granulate, which is dried in a fluidized-bed apparatus (Aeromatic Mod. Strea) with an incoming air temperature of 40–45° C. The granulate, which is dried until constant weight is achieved, is next put in a powder mixer (Turbula Mod. T2A), with the addition of magnesium stearate and colloidal silica, and then mixed for a further 20 minutes. The granulate, lubricated, undergoes the compression phase, as described hereinafter.

1-c-Preparation of Two-Layer Systems (by compression)

The two types of granulate, obtained according to the procedure previously described and according to schemes well known to all those skilled in the sector, are loaded into two loading hoppers of a rotary layer press suitable for producing two-layer tablets (e.g., Manesty Layer-Press, Liverpool, UK). In particular, the granulate described in point 1-a is loaded into the first hopper, whilst the granulate described in point 1-b is loaded into the second hopper.

The layer-press is equipped with rounded circular punches having a diameter of 7.0 mm and a radius of curvature R=10 mm.

The machine is adjusted so as to produce two-layer systems consisting of a first layer weighing 144.0 mg containing the active principle (corresponding to 60 mg of nifedipine), and a second layer weighing 70 mg of slow-hydration barrier granulate.

Proceeding as described previously, two-layer tablets are obtained, each having a mean weight of 214.0 mg and containing 60 mg of active principle.

One part of these non-coated tablets were used for the bio-availability clinical study to check the food effect.

1-d-Dissolution Test

To evaluate the characteristics of release of the active principle by the systems prepared, a USP XXII paddle-type dissolution apparatus, operating at 100 r.p.m., is used, and 1 lit. of pH 6.8 buffer solution consisting or tris-hydroxymethyl-aminomethane 0.1M containing 1% of polysorbate 80 is used as dissolution fluid. The release of the active principle is monitored by means of UV spectrophotometric determination using an automatic sampling and reading system (Beckman).

The results of the tests carried out are shown in Table I.

TABLE I

| Time (h) | % released Non-coated systems |
|---|---|
| 1 | 2.0 |
| 5 | 17.0 |
| 6 | 24.0 |
| 12 | 62.0 |
| 15 | 75.0 |
| 18 | 84.2 |

1-e-Process of Film-Coating of Two-Layer Systems

The tablets obtained as described in the foregoing point 1-c undergo a double film-coating process, there being applied on each of said tablets a film having the following composition:

| | |
|---|---|
| Acrylic and methacrylic acid copolymer (Eudragit L 30 D, Rohm Pharma, Germany) | 10.70 mg |
| Triethyl citrate (Carlo Erba, Milan, Italy) | 1.60 mg |
| Total | 12.30 mg |

The film-coating process is carried out using a revolving pan for fast coating (Manesty Accela-Cota) into which the tablets are poured. Then a 30% aqueous dispersion of the acrylic and methacrylic acid copolymer (Eudragit L 30 D) in which triethyl citrate has been solubilized is sprayed on the tablets, which are kept rotating, by means of an airless spray system. The operation takes place at an incoming air temperature of approximately 40–50° C., according to a technique known to anybody skilled in the sector. In this way, tablets are obtained that are totally coated with a uniform film of the polymeric material referred to above.

2nd Coating

| | |
|---|---|
| Hydroxypropylmethyl cellulose (viscosity 15 cP) | 7.5 mg |
| Lactose | 1.0 mg |
| Titanium dioxide | 0.5 mg |
| Polyethylene glycol 4000 | 1.2 mg |
| Ferric oxide | 0.1 mg |
| Total | 10.3 mg |

The second coating is applied on the tablets according to the procedure described above.

One part of these coated tablets were used for the bioavailability clinical study in order to assess the food effect.

1-*f*-Dissolution Test

In order to evaluate the release characteristics of the finished systems, the USP XXII paddle-type dissolution apparatus was used running at a rate of 100 r.p.m. For the first 5 hours of release, 1 lit of HCl 0.1 M, pH 1.0, in which 1% polysorbate 80 had been solubilized, was used as dissolution fluid. Starting from the 5th hour, the dissolution fluid was replaced by a buffer solution consisting of 0.1M of tris-hydroxy-methylaminomethane, pH 6.8, containing 1% of polysorbate 80. The release of the active principle was monitored by means of UV spectrophotometric determination using an automatic sampling and reading system (Beckman).

The results of the tests carried out are shown in Table II.

TABLE II

| Time (h) | Core + 1 barrier % released |
|---|---|
| 1 | 0.0 |
| 5 | 1.0 |
| 6 | 3.0 |
| 12 | 31.0 |
| 20 | 76.0 |
| 24 | 100.2 |

From Table II it may be noted that the release of the drug from the systems prepared starts only after an initial period of 5 hours (during which, owing to the presence of an acid environment, practically no drug is released); subsequently, in the second phase, which is clearly differentiated from the previous one in that the dissolution fluid has been changed, the drug is released at a controlled rate of approximately 3.2 mg/h. This behaviour fully meets the purposes of the present invention.

1-*g*-In Vivo Study and Assessment of Food Effect—Non-Coated Systems

In order to assess the influence of food on the bioavailability of the drug having the pharmaceutical form under examination, a single-dose cross-over study was carried out on 12 healthy volunteers, by administering the non-coated pharmaceutical form described in Example 1 from point 1-*a* to point 1-*c*.

The experimental protocol envisaged one administration in fasting conditions and, subsequently, after an adequate wash-out period, another administration after a high fat content breakfast.

From each volunteer blood samples were taken up to the 48th hour following on administration. The drug concentration was determined on these samples, employing the validated gas-chromatography procedure.

Table III shows the means of the blood plasma levels.

TABLE III

| Time (h) | Fasting Non-coated tablets | Presence of food Non-coated tablets |
|---|---|---|
| 1 | 5.90 | 2.19 |
| 3 | 18.10 | 41.41 |
| 6 | 18.41 | 67.73 |
| 9 | 16.06 | 44.17 |
| 12 | 22.69 | 31.09 |
| 15 | 22.23 | 29.86 |
| 18 | 18.71 | 21.27 |
| 21 | 17.27 | 18.03 |
| 24 | 17.75 | 13.41 |
| 27 | 18.01 | 12.64 |
| 30 | 16.20 | 8.85 |
| 33 | 12.40 | 6.72 |
| 36 | 10.38 | 4.91 |
| 48 | 5.87 | 1.72 |

From a comparison of the results given in Table III, it emerges clearly that, in the case of non-coated tablets, the absorption of the active principle is considerably influenced by the presence of food. This result is confirmed by the pharmacokinetic parameters (C max) and by the corresponding percentage variations, tabulated in Tables V-a and V-b.

1-*h*-In Vivo Study and Assessment of Food Effect—Coated Systems

In order to assess the influence of food on the bioavailability of the drug having the pharmaceutical form under examination, a single-dose cross-over study was carried out on 12 healthy volunteers, by administering the coated pharmaceutical form described in Example 1 from point 1-*a* to point 1-*e*.

The experimental protocol envisaged one administration in fasting conditions and, subsequently, after an adequate wash-out period, another administration after a high fat content breakfast.

From each volunteer blood samples were taken up to the 48th hour following on administration. The drug concentration was determined on these samples, employing the validated gas-chromatography procedure.

Tables V-a and V-b show the means of the blood plasma levels.

TABLE IV

| Time (h) | Fasting Coated tablets | Presence of food Coated tablets |
|---|---|---|
| 1 | 0.13 | 0.00 |
| 3 | 7.24 | 0.84 |
| 6 | 13.15 | 7.64 |
| 9 | 10.50 | 7.32 |
| 12 | 17.67 | 12.22 |
| 15 | 20.62 | 14.38 |
| 18 | 17.76 | 14.54 |
| 21 | 15.72 | 14.21 |
| 24 | 15.76 | 19.85 |
| 27 | 19.85 | 24.37 |
| 30 | 16.71 | 19.39 |
| 33 | 12.69 | 16.37 |
| 36 | 11.16 | 15.63 |
| 48 | 4.71 | 9.11 |

From a comparison of the results given in Table IV, it emerges clearly that, in the case of coated tablets, the absorption of the active principle is not influenced by the presence of food. This result was confirmed by the pharmacokinetic parameters (C max) and by the corresponding percentage variations, tabulated in Tables V-a and V-b.

Tables V-a and V-b show the pharmacokinetic data (max plasma concentration and area under the curve) for the administration of non-coated and coated tablets, in fasting conditions and after intake of a standardized breakfast.

TABLE V-a

Example 1 - Nifedipine 60 mg
Pharmacokinetic parameters (C max) -
In vivo study on effect of presence of food

|  | C max (ng/ml) Fasting | C max (ng/ml) Presence of food | Percentage difference |
|---|---|---|---|
| Non-coated system | 28.49 | 91.72 | 68.9 |
| Coated system | 24.38 | 27.40 | 11.0 |

TABLE V-b

Example 1 - Nifedipine 60 mg
Area under curve (AUC) - In vivo study on effect of presence of food

|  | AUC Fasting | AUC Presence of food | Percentage difference |
|---|---|---|---|
| Non-coated system | 656.6 | 793.7 | 17.3 |
| Coated system | 563.8 | 617.0 | 8.6 |

From a comparison between the results given in Table III and those given in Table IV, as well as from the pharmacokinetic parameters tabulated in Tables V-a and V-b, it emerges clearly that, only in the case of coated tablets, is absorption of the active principle unaffected by the presence of food. In particular, it should be pointed out that the presence of the coating does not significantly affect the AUC values either in a fasting condition or when food is present (a percentage difference of below 25% is considered acceptable), whereas a highly significant effect emerges on maximum blood plasma concentrations. In fact, from a percentage difference of 68.9% in the case of non-coated systems, the difference drops to 11% in the case of administration of the systems claimed in the present patent application. A percentage difference of over 25% is considered significant as regards the influence of food on absorption of the drug.

The above result fully meets the purposes of the present invention.

EXAMPLE 2

Preparation of a batch of 5,000 tablets, of the type shown in FIG. 1, containing 50 mg of ketoprofen as active principle.

2-a-Preparation of Non-Coated Tablets

Using known techniques, a batch of tablets was prepared having the following composition per unit:

| Ketoprofen | 50.00 mg |
|---|---|
| Hydroxypropylmethyl cellulose | 51.90 mg |
| Lactose monohydrate | 51.90 mg |
| Glyceryl behenate | 10.80 mg |
| Polyvinyl pyrrolidone | 9.00 mg |
| Yellow iron oxide | 0.20 mg |
| Magnesium stearate | 1.80 mg |
| Colloidal silica | 1.40 mg |
| Total | 177.00 mg |

Tablets were produced, each having a mean weight of 177.0 mg and containing 50 mg of active principle. The layer-press was equipped with rounded circular punches having a diameter of 7.0 mm and a radius of curvature R=10 mm.

2-b-Film-Coating Process

The tablets obtained as described in the foregoing point 2-a undergo a film-coating process, there being applied on each of said tablets a film having the following composition:

| Acrylic and methacrylic acid copolymer (Eudragit L 30 D Rohm Pharma, Germany) | 2.5 mg |
|---|---|
| Polyethylene glycol 6000 | 0.4 mg |
| Tatcum | 3.5 mg |
| Titanium dioxide | 2.2 mg |
| Yellow iron oxide | 0.1 mg |
| Total | 8.7 mg |

The film-coating process is carried out by means of mist-spraying of the aqueous dispersion of the polymeric material in an Accela-Cota revolving pan, according to the known technique.

One part of these coated tablets were used for the bio-availability clinical study in order to assess the food effect.

2-c-Preparation of Systems Containing 200 mg of Ketoprofen

Using a suitably equipped capping machine (Type MG 2—Osteria Grande, Italy), 4 coated tablets, obtained as described above, were introduced into type-00 hard gelatine capsules, obtaining systems containing altogether 200 mg of ketoprofen. These systems underwent the subsequent check on dissolution of the active principle.

2-d-Dissolution Test

In order to evaluate the release characteristics of the finished systems, the USP XXII paddle-type dissolution apparatus was used running at a rate of 100 r.p.m. For the first 4 hours of release, 1 lit of a 0.1M hydrochloric acid solution (pH 1.0) was used operating at 37° C. Starting from the 4th hour, the dissolution fluid was replaced by a buffer solution (pH 7.5) consisting of tris-hydroxymethylaminomethane, sodium chloride and NaOH.

The release of the active principle was monitored by means of UV spectrophotometric determination at 260 nm using an automatic sampling and reading system (Spectracomp 602 manufactured by Advanced Products, Milan).

The results of the tests carried out are shown in Table VI.

TABLE VI

| Time (h) | % released Coated systems |
|---|---|
| 1 | 0.0 |
| 4 | 0.0 |
| 5 | 7.0 |
| 6 | 13.0 |
| 7 | 19.0 |
| 8 | 25.0 |
| 10 | 42.0 |
| 12 | 59.0 |
| 14 | 72.0 |
| 16 | 83.0 |
| 18 | 91.0 |
| 20 | 96.0 |
| 24 | 100.0 |

From Table VI it may be noted that the release of the drug from the coated systems starts only after an initial period of 4 hours (during which, owing to the presence of an acid environment, practically no drug is released); subsequently, in the second phase, which is clearly differentiated from the previous one in that the dissolution fluid has been changed, the ketoprofen is released at a controlled rate. This behaviour fully meets the purposes of the present invention.

2-e-In Vivo Study and Assessment of Food Effect

In order to assess the influence of food on the bioavailability of the drug having the pharmaceutical form under examination, a single-dose cross-over study was carried out on 11 healthy volunteers, by administering a capsule containing 4 coated tablets, prepared as described in point 2-c above.

The experimental protocol envisaged one administration in fasting conditions and another administration after a high fat content breakfast.

From each volunteer blood samples were taken up to the 30th hour following on administration. The drug concentration was determined on these samples, using a validated procedure.

Table VII shows the means of the blood plasma levels.

TABLE VII

| Time (h) | Fasting Coated tablets | Presence of food Coated tablets |
| --- | --- | --- |
| 1 | 0.11 | 0.00 |
| 2 | 0.67 | 0.01 |
| 3 | 1.50 | 0.15 |
| 4 | 1.97 | 0.79 |
| 5 | 1.93 | 1.31 |
| 6 | 2.25 | 2.51 |
| 8 | 1.81 | 2.31 |
| 10 | 1.98 | 1.90 |
| 12 | 2.26 | 2.53 |
| 14 | 1.70 | 2.31 |
| 18 | 0.95 | 1.17 |
| 22 | 0.49 | 1.16 |
| 26 | 0.24 | 0.76 |
| 30 | 0.14 | 0.52 |

From a comparison of the results given in Table VII, it emerges clearly that, in the case of coated tablets, the absorption of the active principle is not markedly influenced by the presence of food. This result is confirmed by the pharmacokinetic parameters (C max) and by the corresponding percentage variations, tabulated in Table VIII.

Table VIII shows the pharmacokinetic data (max plasma concentration and area under the curve) for the administration of coated tablets, in fasting conditions and after intake of a standardized breakfast.

TABLE VIII

Example 2 - ketoprofen 200 mg
Pharmacokinetic parameters (C max - AUC) -
In vivo study of effect of presence of food

|  | Fasting | Presence of food | Percentage difference |
| --- | --- | --- | --- |
| C max (ng/ml) | 2.90 | 3.80 | 23.7 |
| AUC | 32.53 | 38.95 | 16.5 |

From a comparison of the results given in Table VII and from the pharmacokinetic parameters tabulated in Table VIII, it emerges clearly that, only in the case of coated tablets, the absorption of the active principle is unaffected by the presence of food. In particular, it should be pointed out that the presence of the coating does not significantly affect the AUC values either in a fasting condition or when food is present (a percentage difference of below 25% is considered acceptable), whereas a highly significant effect emerges on maximum blood plasma concentrations. In fact, in the case of administration of the coated systems claimed in the present patent application, there is a percentage difference of 23.7%. A percentage difference of over 25% is considered significant as regards the influence of food on absorption of the drug.

The above result fully meets the purposes of the present invention.

We claim:

1. A pharmaceutical tablet designed for the controlled release of active principles which exhibits a different biological absorption rate in the presence and in the absence of food, which comprises: a core having one or more layers, at least one of which serves as a vehicle for the active principle, while the other layer or layers, selected from the group consisting of erodible, gellable, and erodible and gellable hydrophilic polymers, function as a barrier, being initially impermeable to the passage of the active principle and said tablet being completely coated with one or more films of a biocompatible and biodegradable polymeric material, at least one of said films being of a gastro-resistant and entero-soluble material selected from the group consisting of: cellulose acetophthalate, cellulose acetopropionate, cellulose trimellitate, copolymers of methacrylic and acrylic acids, copolymers of methacrylic acid and methylmethacrylate and methylvinylether-maleic anhydride copolymers.

2. The pharmaceutical tablet according to claim 1, wherein said tablet has a cylindrical shape with a diameter of from 2 to 13 mm and a thickness of from 2 to 10 mm.

3. The pharmaceutical form consisting of two or more tablets according to claim 1, and contained in hard-gelatine capsules to provide a vehicle for a quantity of active principle corresponding to a single dose.

4. The pharmaceutical tablet according to claim 1, wherein the active principles showing different rates of absorption in the presence and in absence of food are selected from the group consisting of steroidal anti-inflammatory drugs, non-steroidal anti-inflammatory drugs (NSAIDs), sleep-inducing drugs and tranquillizers, active principles for the prevention of attacks of angina, antihistamines, and anti-asthmatic drugs, β-lactam antibiotics alone or in association with β-lactamase inhibitors.

5. The pharmaceutical tablet according to claim 1, wherein the active principle is nifedipine.

6. The pharmaceutical tablet according to claim 1, wherein the active principle is ketoprofen.

7. The pharmaceutical tablet according to claim 1, wherein said vehicled active principles account for 1.0% to 90% of the weight of the tablet.

8. The pharmaceutical tablet according to claim 1, wherein in the preparation of the core containing the active principle, polymeric substances are used, selected from the group consisting of polyvinyl pyrrolidone, cross-linked polyvinyl pyrrolidone, hydroxypropyl cellulose, hydroxypropylmethyl cellulose, carboxymethyl cellulose and derivatives thereof, cross-linked sodium carboxymethyl cellulose, carboxymethylstarch, potassium methacrylate-divinylbenzene copolymer, and polyvinyl alcohols.

9. The pharmaceutical tablet according to claim 8, wherein said polymeric substances account for about 5% to about 90% of the total weight of the tablet.

10. The pharmaceutical tablet according to claim 1, wherein, in order to favor the penetration of water and/or aqueous fluids into the tablet, lactose is introduced as hydrophilic diluent in the formulation thereof.

11. The pharmaceutical tablet according to claim 1, wherein glycerol behenate is used as a hydrophobic diluent to slow the penetration of water and/or aqueous fluids into the tablet.

12. The pharmaceutical tablet according to claim 1, wherein said coating materials may be applied on the tablet by a method selected from conventional film-coating processes, by using aqueous solutions or dispersions mist-sprayed in a revolving pan, or in a fluidized bed.

13. The pharmaceutical tablet according to claim 12, wherein one or more layers having different compositions are applied.

14. The pharmaceutical tablet according to claim 1, wherein the coating films comprise plasticizing materials selected from the group, consisting of triethyl citrate, diethyl phthalate, diacetin, triacetin, dibutyl phthalate, dibutyl tartrate, tributyl acetate, castor oil, cetyl alcohol, cetylstearyl alcohol, fatty acids, glycerides and triglycerides and polyoxyethylene glycols with different molecular weights, normally chosen within the 200–20,000 range.

15. The pharmaceutical form according to claim 14, wherein said plasticizing materials may be present in a percentage of from 10% to 20% with respect to the polymeric material of the coating.

* * * * *

UNITED STATES PATENT AND TRADEMARK OFFICE
CERTIFICATE OF CORRECTION

PATENT NO. : 6,027,748
DATED : February 22, 2000
INVENTOR(S) : Ubaldo Conte, et al.

It is certified that error appears in the above-identified patent and that said Letters Patent is hereby corrected as shown below:

Column 6, line 44, delete "core containing the active ingredient" and insert --coating layer--.

Column 6, line 45, delete "coating layer" and insert --core containing the active ingredient--.

Signed and Sealed this

Thirteenth Day of June, 2000

Attest:

Q. TODD DICKINSON

*Attesting Officer*  *Director of Patents and Trademarks*